United States Patent [19]

Luthy

[11] Patent Number: 4,837,421
[45] Date of Patent: Jun. 6, 1989

[54] FRAGRANCE DISPENSING APPARATUS

[75] Inventor: Chella Luthy, New York, N.Y.

[73] Assignee: Creative Environments, Inc., New York, N.Y.

[21] Appl. No.: 123,669

[22] Filed: Nov. 23, 1987

[51] Int. Cl.$^4$ ............................................. H05B 3/48
[52] U.S. Cl. .................................... 219/272; 219/274; 219/275
[58] Field of Search ............... 219/271, 272, 273, 274, 219/275, 276, 492

[56] References Cited

U.S. PATENT DOCUMENTS

| | | | |
|---|---|---|---|
| 2,513,919 | 7/1950 | Costello | 219/272 |
| 2,611,068 | 9/1952 | Wellens | 219/272 |
| 2,690,500 | 9/1954 | Winberg | 219/272 |
| 2,692,327 | 10/1954 | Avrigan | 219/272 |
| 4,184,099 | 1/1980 | Lindauer | 313/315 |
| 4,214,146 | 7/1980 | Schimanski | 219/275 |
| 4,391,781 | 7/1983 | Van Lit | 219/274 |
| 4,486,648 | 12/1984 | Grasso | 219/492 |
| 4,631,387 | 12/1986 | Glucksman | 219/275 |
| 4,668,854 | 5/1987 | Swan | 219/273 |

Primary Examiner—Teresa J. Walberg
Attorney, Agent, or Firm—Karl F. Milde, Jr.

[57] ABSTRACT

A fragrance dispensing apparatus of the type which releases a fragrance from a solid polyamide resin body includes a volatile substance such as perfume oils, insecticides, odorants, bactericides and animal repellants. The apparatus includes a housing having at least one opening therein and disposed adjacent the composition for transferring fragrance therefrom to the other side of the housing. A heating resistor is provided in the housing for maintaining an elevated temperature. A heater plate formed of sheet metal is arranged in the housing in thermally conductive relationship with the heating resistor. The heater plate is configured to at least partially surround and contact the resin body.

15 Claims, 5 Drawing Sheets

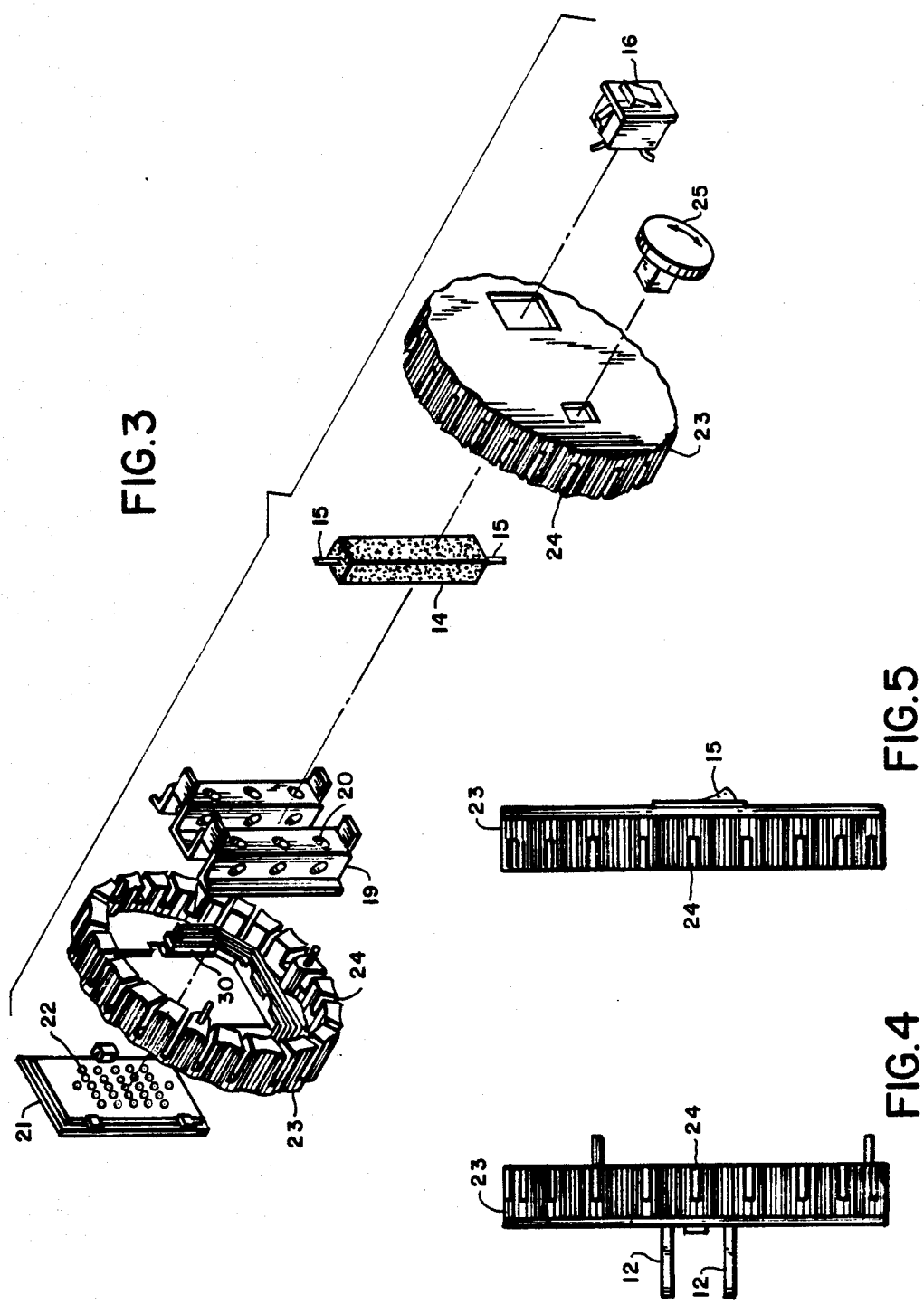

FRAGRANCE DISPENSING APPARATUS

This invention relates to fragance dispensing apparatus and, more prticularly, to such apparatus of the type which releases a fragrance from a body of a volatile substance selected from the group consisting of perfume oils, insecticides, odorants, bactericides and animal repellants.

U.S. Pat. No. 4,184,099-Lindauer et al relates to a light bulb having thereon a composition for slow release of volatile ingredients at high temperature. Such a light bulb is subject to the disadvantage that it is easily breakable and requires a light bulb socket for operation.

It is an object of the invention to provide a new and improved fragrance dispensing apparatus which avoids one or more of the disadvantages of prior such apparatus.

It is another object of the invention to provide a new and improved fragrance dispensing apparatus which may be readily utilized in connection with an electrical source without requiring a light bulb socket.

It is another object of the invention to provide a new and improved fragrance dispensing apparatus which is relatively unbreakable.

It is another object of the invention to provide a new and improved fragrance dispensing apparatus which is readily portable.

In accordance with the invention, fragrance dispensing apparatus comprises, in combination, means adapted to be selectively connected to a source of voltage. The apparatus also includes resistance heating means, electrically coupled to the connection means, for maintaining a substantially constant temperature in the range of 40°–120° C. The apparatus also includes means disposed in thermally coupled relationship to the heating means for holding a composition for slow release of volatile ingredients at an elevated temperature. The composition comprises a thermoplastic polyamide resin body consisting essentially of from 35% up to 70% by weight of the body of a volatile substance selected from the group consisting of perfume oils, insecticides, ororants, bactericides and animal repellants. The apparatus also includes a housing for the resistance heating means and the holding means and having at least one opening therein and disposed adjacent the composition for allowing fragrance to be transferred from said composition to the other side of the housing.

For a better understanding of the invention, together with other and further objects thereof, reference is made to the following description, taken in connection with the accompanying drawings, and its scope will be pointed out in the appended claims.

Referring now to the drawings:

FIG. 3 is an exploded view of the FIG. 1 apparatus;

FIG. 4 is a side view in elevation of the rear portion of the FIG. 1 apparatus;

FIG. 5 is a side view in elevation of the front portion of the FIG. 1 apparatus;

FIG. 9 is an end view of the FIG. 8 plate;

Figure 1:
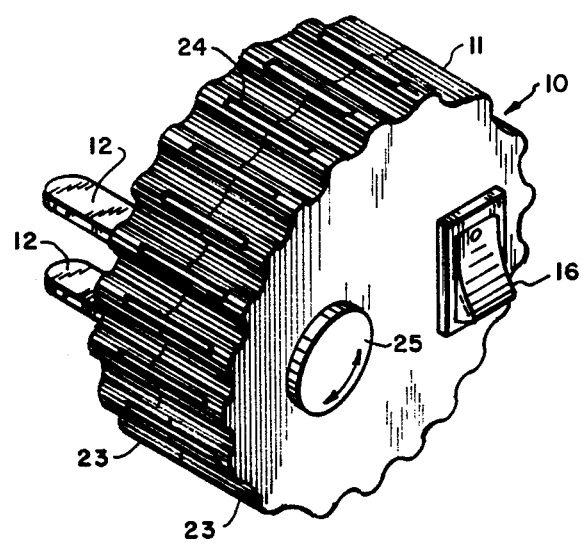
FIG. 1 is a perspective view of fragrance dispensing apparatus constructed in accordance with the invention.

Referring now more particularly to FIG. 1 of the drawings, there is represented a fragrance dispensing apparatus 10 comprising a housing 11 having at least one opening therein and formed into a housing in the FIG. 1 embodiment. The apparatus includes means 12 adapted to be selectively connected to a source of voltage. The means 12 preferably includes an electrical plug. The apparatus also includes resistance heating means 13 represented schematically in FIG. 2 electrically coupled to the connection means 12 for maintaning a substantially constant temperature in the range of 40°–120° C.

Referring to FIG. 3, the resistance heating means 13 preferably is included within, and more preferably centrally within, a composition 14 preferably in the form of a bar for slow release of volatile ingredients at an elevated temperature. Electrical connection leads 15 extend from the resistance heating means 13 within the bar 14. The resistance heating means is operative to maintain a substantially constant temperature preferably in the range of 50°–100° C. and, more preferably, in the range of 70°–90° C. It is particularly desirable that the resistance heating means maintain a substantially constant of approximately 80° C.

Figure 2:
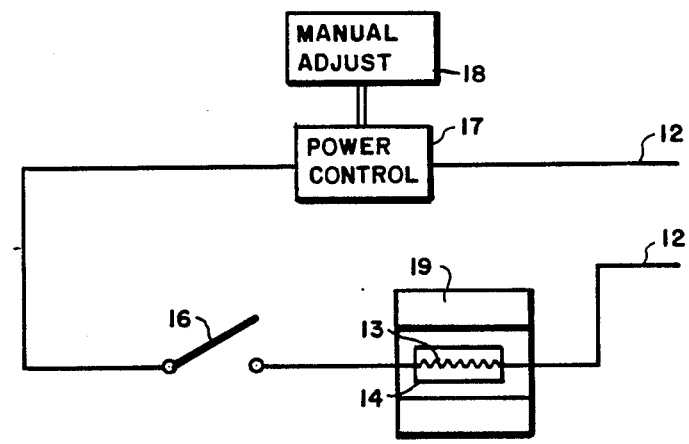
FIG. 2 is a schematic diagram of the FIG. 1 apparatus.
Figure 6:
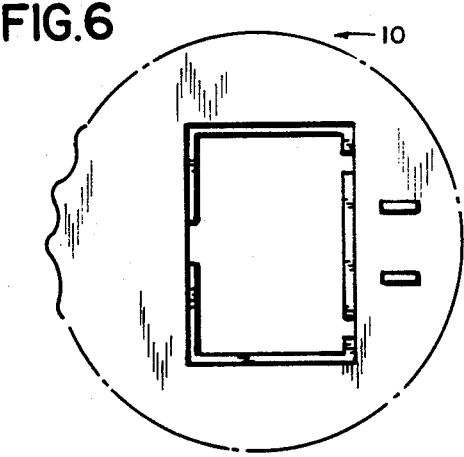
FIG. 6 is a rear view, partly schematic, of the FIG. 1 apparatus, with a back plate removed.
Figure 7:
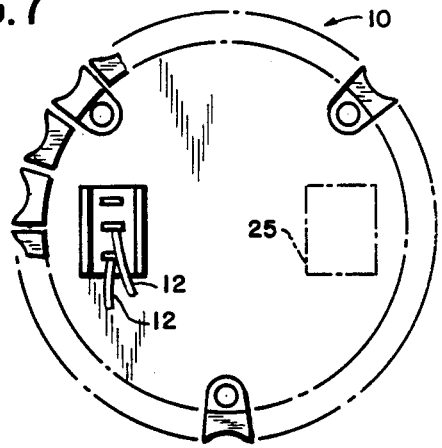
FIG. 7 is a view of the inside of the front portion of the FIG. 1 apparatus.
Figure 8:
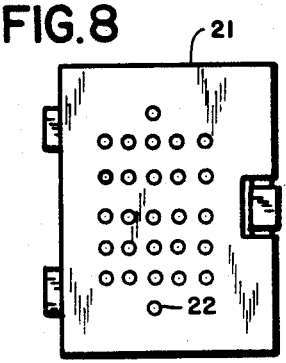
FIG. 8 is a plan view of the outer side a back plate removed from the FIG. 6 portion.
Figure 9:
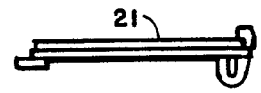
FIG. 9 is a side view of the FIG. 8 plate.
Figure 10:
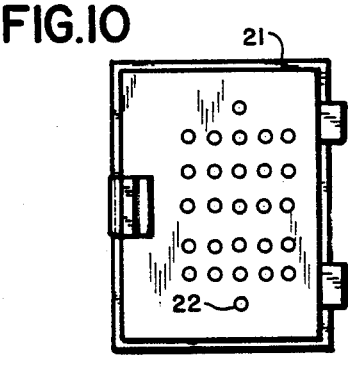
FIG. 10 is a view of the inner side of the FIG. 8 plate.

As previosuly mentioned, the connection means includes the electrical plug 12, and the connection means preferably also includes an electrical on/off switch 16 represented schematically in FIG. 2. The connection means preferably also includes control means represented schematically in FIG. 2 as a power control 17 having a manual adjustment 18 for producing a pulsed voltage with a variable duty cycle.

Figure 11:
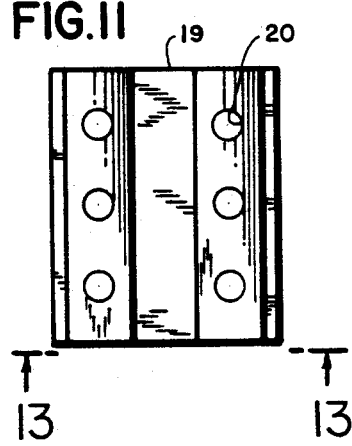
FIG. 11 is a plan view of the holding means of the FIG. 1 apparatus.
Figure 12:
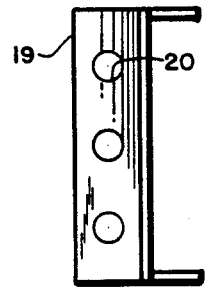
FIG. 12 is a side elevational view of the FIG. 11 holding means.
Figure 13:
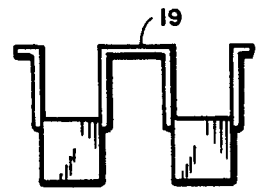
FIG. 13 is an end view in elevation of the FIG. 11 holding means.

The holding means preferably includes a thermally conductive heater plate 19 of aluminum having openings 20 therein. The housing 11 preferably includes a back plate 21 with a plurality of openings 22 therein and having a side wall 23 having openings therein preferably in the form of slots 24 for air communiation between the composition 14 and the other side of the back plate and side wall. The housing preferably comprises non-conductive plastic and transfers fragrance from the composition 14 through openings 22 and 24 to the other side of the wall 23. As represented in FIGS. 6, 8, 9 and 10, the back plate 21 can be easily seated in the rear portion of the housing and self-fastened in place by a resilient tab. The heater plate 19 of FIGS. 11, 12 and 13 may be fastened in place by a suitable means, for example, by pressing resiliently outwardly against ridges 30 of the FIG. 3 housing.

If desired, a suitable light bulb may be connected across the input plug and a translucent light aperture plug 25 may be included to give a visual indication that the plug 25 is connected to an electric power source.

The composition 14 comprises a thermoplastic polymide resin body consisting essentially of from 35% up to 70% by weight of the body of a volatile substance selected from the group consisting of perfume oils, insecticides, odorants, bactericides and animal repellants. A suitable composition is of the Versalon ® type. described in U.S. Pat. No. 4,184,099- Lindauer et al. Versalon ® is a trademark of the General Mills Corporation of Minneapolis, Minn.

Figure 14:
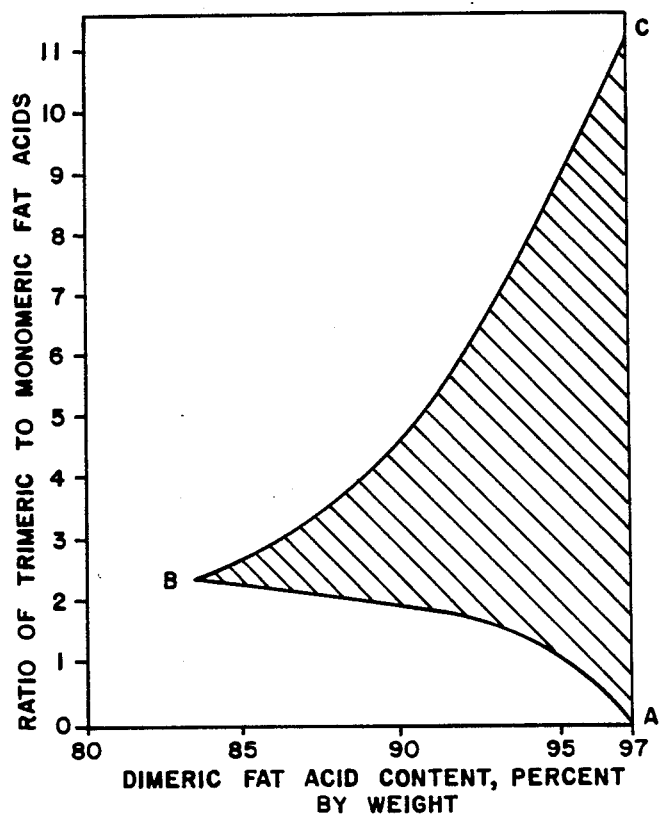
FIG. 14 is a graphical representation showing the preferred combination in the Versalon ® type polyamide resins useful in our invention of dimer content and trimer:monomer ratio.

Referring to FIG. 14, the area bounded substantially within the curve ABC includes those polyamides, defined as Versalon ® which are considered satisfactory for the purposes of carrying out the present invention.

Figure 15:
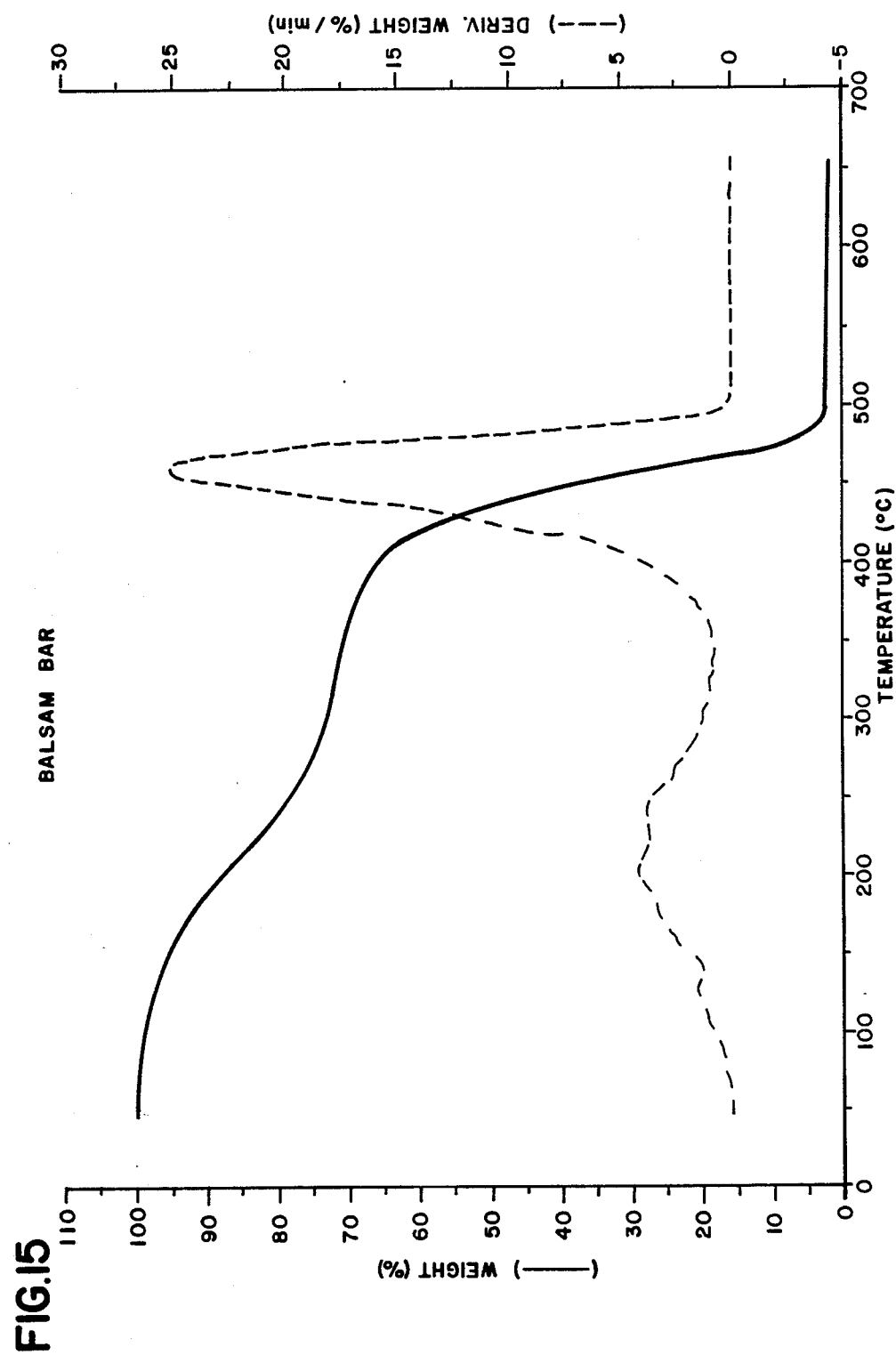
FIG. 15 is a graph representing weight (%) of a balsam bar composition vs. temperature and the derivative of weight (% per minute) of the composition vs. temperature.

Referring to FIG. 15, it can be seen that the composition vaporizes relatively slowly at temperature in the range of 40°-120° C.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Fragrance dispensing apparatus comprising, in combination;

means adapted to be selectively connected to a source of voltage;

resistance heating means, electrically coupled to said connection means, for maintaining a substantially constant temperature in the range of 40°-120° C.;

means disposed in thermally coupled relationship to said heating means, for holding a composition for slow release of volatile ingredients at an elevated temperature, said composition comprising a solid, thermoplastic polyamide resin body consisting essentially of from 35 percent up to 70 percent by weight of said body of a volative substance selected from the group consisting of perfume oils, insecticides, odorants, bactericides and animal repellants, said solid resin body being in the form of an elongate block, and said holding means comprising a thermally conductive heater plate formed of sheet metal, said heater plate being configured to at least partially surround and contact said block along substantially its entire length on one side and being in thermally coupled relationship to said heating means; and a housing for holding and surrounding said resistance heating means and said holding means and having at least one opening therein and disposed adjacent said composition for allowing fragrance to be transferred from said composition to the outside of said housing.

2. The dispensing apparatus defined in claim 1, wherein said resistance heating means is operative to maintain a substantially constant temperature in the range of 50°-100° C.

3. The dispensing apparatus defined in claim 2, wherein said resistanve heating means is operative to maintain a substantially constant temperature in the range of 70°-90° C.

4. The dispensing apparatus defined in claim 3, wherein said resistance heating means is operative to maintain a substantially constant temperature of approximately 80° C.

5. The dispensing apparatus defined in claim 1, wherein said connection means includes an electrical plug.

6. The dispensing apparatus defined in claim 5, wherein said connection means includes an electrical on/off switch.

7. The dispensing apparatus defined in claim 1, wherein said connection means includes control means for producing a pulsed voltage with a variable duty cycle.

8. The dispensing apparatus defined in claim 1, wherein said holding means includes a thermally conductive heater plate.

9. The dispensing apparatus defined in claim 8, wherein said heater plate is made of aluminum.

10. The dispensing apparatus defined in claim 1, in which said housing has a back plate with a plurality of openings therein and has a side wall with openings therein for air communication between said composition and the other side of said back plate and side wall.

11. The dispensing apparatus defined in claim 1, wherein said heater plate is serpentine in cross section.

12. The dispensing apparatus defined in claim 1, wherein said heater plate has a plurality of openings therethrough for the passage of air past said solid resin body.

13. The dispensing apparatus defined in claim 1, wherein said heater plate is configured to surround said solid resin body on three lateral sides thereof.

14. The dispensing apparatus defined in claim 1, wherein said connection means include an electrical plug having at least one prong that is attached to said housing, said at least one opening comprising a plurality of openings extending in a direction transverse to the axis of said plug, whereby said openings are adapted to allow the upward passage of air through said housing when said plug is inserted horizontal in a plug receptable.

15. The dispensing apparatus defined in claim 14, wherein said housing has a round vertical, external profile when oriented with the axis of said plug arranged horizontally, and wherein said openings are arranged around the circumference of said housing.

* * * * *